(12) United States Patent
Ok et al.

(10) Patent No.: US 11,766,548 B2
(45) Date of Patent: Sep. 26, 2023

(54) PHOTOTHERAPEUTIC NEEDLE PATCHES AND METHODS OF MANUFACTURING THE SAME

(71) Applicants: KOREA INSTITUTE OF SCIENCE AND TECHNOLOGY, Seoul (KR); Industry-University Cooperation Foundation Hanyang University ERICA Campus, Ansan-si (KR)

(72) Inventors: Myoung-Ryul Ok, Seoul (KR); So Yeon Kim, Seoul (KR); Yoon Ki Joung, Seoul (KR); Yu Chan Kim, Seoul (KR); Hyun Kwang Seok, Seoul (KR); Hyung-Seop Han, Seoul (KR); Hojeong Jeon, Seoul (KR); Hyunseon Seo, Seoul (KR); Inho Kim, Seoul (KR); Kyoung Won Park, Seoul (KR); Yongwoo Chung, Seoul (KR); Jaekyun Kim, Ansan-si (KR)

(73) Assignees: KOREA INSTITUTE OF SCIENCE AND TECHNOLOGY, Seoul (KR); INDUSTRY-UNIVERSITY COOPERATION FOUNDATION HANYANG UNIVERSITY ERICA CAMPUS, Gyeonggi-Do (KR)

(*) Notice: Subject to any disclaimer, the term of this patent is extended or adjusted under 35 U.S.C. 154(b) by 228 days.

(21) Appl. No.: 17/153,969

(22) Filed: Jan. 21, 2021

(65) Prior Publication Data
US 2021/0220631 A1 Jul. 22, 2021

(30) Foreign Application Priority Data

Jan. 21, 2020 (KR) .................. 10-2020-0008099
Jan. 15, 2021 (KR) .................. 10-2021-0005886

(51) Int. Cl.
*A61M 37/00* (2006.01)
*A61N 5/06* (2006.01)

(52) U.S. Cl.
CPC ......... *A61M 37/0015* (2013.01); *A61N 5/062* (2013.01); *A61M 2037/0023* (2013.01); *A61M 2037/0053* (2013.01)

(58) Field of Classification Search
CPC ...... A61M 37/0015; A61M 2037/0023; A61M 2037/0053; A61N 5/062; A61N 2005/0612; A61N 5/0616
See application file for complete search history.

(56) References Cited

U.S. PATENT DOCUMENTS

| | | | | |
|---|---|---|---|---|
| 2002/0045907 A1* | 4/2002 | Sherman | ............ | A61B 17/205 606/131 |
| 2009/0048557 A1* | 2/2009 | Yeshurun | ............ | A61B 18/203 604/20 |

FOREIGN PATENT DOCUMENTS

| KR | 10-2019-0080325 A | 7/2019 |
|---|---|---|
| KR | 10-2019-0136727 A | 12/2019 |

OTHER PUBLICATIONS

Korean Office Action for KR Application No. 10-2021-0005886 dated Nov. 8, 2022.

* cited by examiner

*Primary Examiner* — Amber R Stiles
(74) *Attorney, Agent, or Firm* — CANTOR COLBURN LLP

(57) ABSTRACT

Provided are phototherapeutic needle patches usable for phototherapy by using needle patches capable of injecting drugs or cosmetic substances to patients, and methods of manufacturing the same. A phototherapeutic needle patch may include a patch body attachable to skin of a patient, at least one microneedle protruding from the patch body, one (Continued)

end of the microneedle configured to deliver a drug through stratum corneum of the skin to inner tissues of the skin, and light grooves formed in a concave shape along a length direction of the microneedle in such a manner that therapeutic light radiated from a light source for phototherapy easily penetrates into the skin along the microneedle.

10 Claims, 19 Drawing Sheets

PHOTOTHERAPEUTIC NEEDLE PATCHES AND METHODS OF MANUFACTURING THE SAME

CROSS-REFERENCE TO RELATED PATENT APPLICATIONS

This application claims the benefit of and priority to Korean Patent Application No. 10-2020-0008099, filed on Jan. 21, 2020 and Korean Patent Application No. 10-2021-0005886, filed on Jan. 15, 2021, in the Korean Intellectual Property Office, respectively, the disclosures of which are incorporated herein in their entirety by reference.

BACKGROUND

1. Field

The present invention relates to phototherapeutic needle patches and methods of manufacturing the same and, more particularly, to phototherapeutic needle patches usable for phototherapy by using needle patches capable of injecting drugs or cosmetic substances to patients, and methods of manufacturing the same.

2. Description of the Related Art

Microneedles refer to a system for physically making tiny holes in the stratum corneum of the skin and delivering a drug through the holes, and may deliver a drug about 100 or more times faster than existing transdermal delivery systems. Currently used or developed microneedles may be divided into a solid type by which the skin is punctured and a drug is applied thereto, and a type by which a drug is applied to needles, i.e., a dissolving type by which a drug is included in needles or a coated type by which a drug is coated on needle surfaces.

In general, microneedles are used to deliver an active substance such as a drug or vaccine into a living body or to detect analytes in the body for biopsy. Delivery of a pharmacologically or chemically active substance by using microneedles is aimed to deliver the active substance through the skin instead of the circulatory system such as blood vessels or lymphatic vessels. Therefore, the microneedles need to have a sufficient physical strength to penetrate through the skin without causing much pain. The microneedles may be applied to the skin for a short time to reduce pain and, in this case, the active substance needs to be rapidly delivered.

SUMMARY

However, according to the above-described existing microneedles, a long time may be taken until the drug included in or coated on the needles penetrates inner tissues of the skin, and thus a patient may feel pain. In addition, when phototherapy is used to maximize a therapeutic effect of the injected drug, light may not penetrate deeply into the skin through the microneedles and thus the therapeutic effect may not be greatly increased.

The present invention provides phototherapeutic needle patches capable of inducing a drug to effectively and rapidly penetrate into inner tissues of the skin, and of inducing light to effectively penetrate into the inner tissues of the skin together with the drug through optical paths formed in needle surfaces to maximize a therapeutic effect for a patient due to interaction between medication and phototherapy, and methods of manufacturing the same. However, the scope of the present invention is not limited thereto.

According to an embodiment of the present invention, a phototherapeutic needle patch includes a patch body attachable to skin of a patient, at least one microneedle protruding from the patch body, one end of the microneedle configured to deliver a drug through stratum corneum of the skin to inner tissues of the skin, and light grooves in a concave shape disposed along a length direction of the microneedle in such a manner that therapeutic light radiated from a light source for phototherapy easily penetrates into the skin along the microneedle.

The phototherapeutic needle patch may further include slots formed by piercing portions of the patch body and portions of the microneedle in a slot shape and connected to ends of the light grooves in such a manner that the therapeutic light easily reaches the light grooves formed in the microneedle.

The light grooves may be formed in one or more of the at least one microneedle.

The microneedle may be gradually reduced in width from bases connected to the patch body toward tips in a pointed shape to easily penetrate through the stratum corneum of the skin.

The light grooves may be formed by grooving the microneedle in a thickness direction by using laser processing.

The light grooves may have a width less than a depth to prevent tissues of the skin from filling the light grooves and blocking optical paths of the therapeutic light.

The light grooves may include protrusions protruding from both sides of the light grooves and formed due to solidification of a metal material melted in vicinity of the light grooves during the laser processing.

The light grooves may contain the drug.

The patch body may include an adhesive sheet on a surface in contact with the skin so as to be adherable to the skin.

A plurality of microneedles may be disposed along both sides of the patch body.

The microneedle may be formed by bending at least a part of the patch body at a side of a through-hole that is disposed in the patch body.

According to another embodiment of the present invention, a method of manufacturing a phototherapeutic needle patch includes a blanking step for forming a planar shape of a patch body and at least one microneedle by blanking out a certain shape from a plate-shaped material, a light groove forming step for forming light grooves along a length direction of the microneedle, and a bending step for forming the microneedle in a direction perpendicular to the patch body by bending portions connected between the patch body and the microneedle.

The method may further include a piercing step for piercing portions of the patch body and portions of the microneedle in a slot shape, before or after the light groove forming step.

In the light groove forming step, the light grooves may be formed by grooving the microneedle in a thickness direction by using laser processing.

In the light groove forming step, protrusions protruding from both sides of the light grooves may be formed due to solidification of a metal material melted in vicinity of the light grooves during the laser processing.

BRIEF DESCRIPTION OF THE DRAWINGS

The above and other features and advantages of the present invention will become more apparent by describing in detail embodiments thereof with reference to the attached drawings in which.

DETAILED DESCRIPTION

Figure 1:
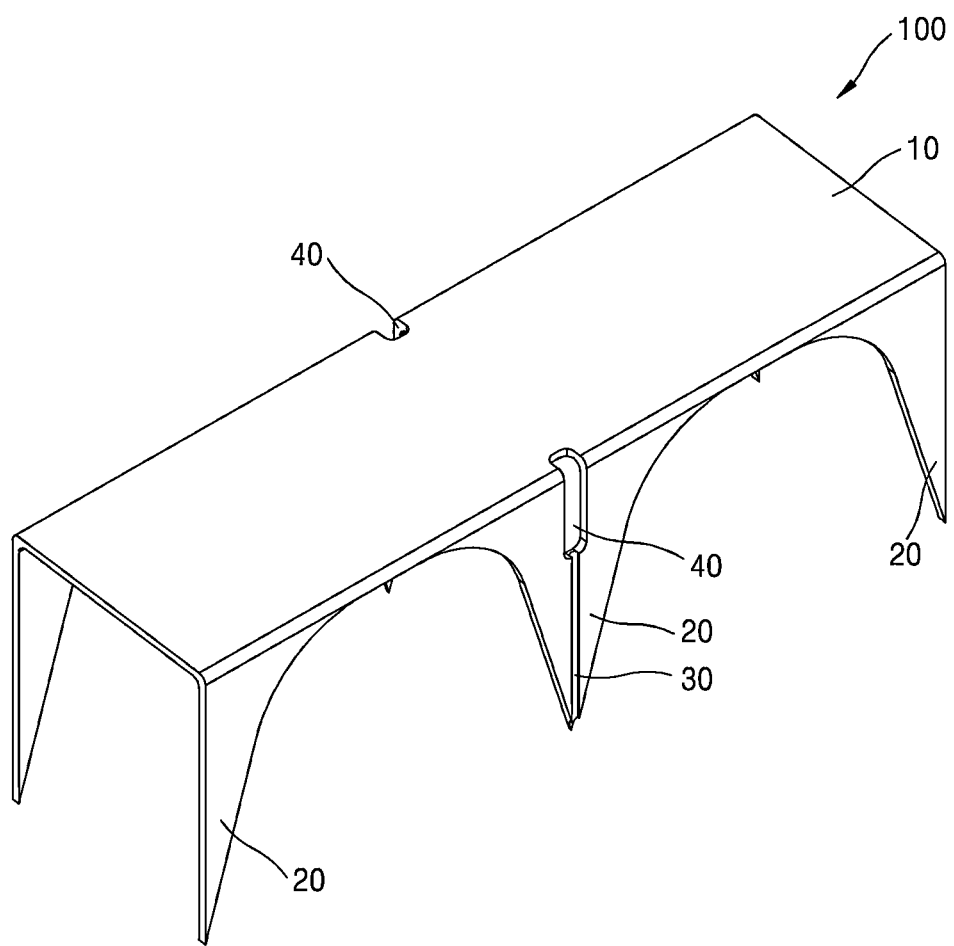
FIG. 1 is a perspective view of a phototherapeutic needle patch according to an embodiment of the present invention.

Hereinafter, the present invention will be described in detail by explaining embodiments of the invention with reference to the attached drawings.

The invention may, however, be embodied in many different forms and should not be construed as being limited to the embodiments set forth herein; rather, these embodiments are provided so that this disclosure will be thorough and complete, and will fully convey the concept of the invention to one of ordinary skill in the art. In the drawings, the thicknesses or sizes of layers are exaggerated for clarity or convenience of explanation.

Embodiments of the invention are described herein with reference to schematic illustrations of idealized embodiments of the invention. As such, variations from the shapes of the illustrations as a result, for example, of manufacturing techniques and/or tolerances, are to be expected. Thus, the embodiments of the invention should not be construed as limited to the particular shapes of regions illustrated herein, but are to include deviations in shapes that result, for example, from manufacturing.

A phototherapeutic needle patch according to a technical idea of the present invention includes a patch body and at least one microneedle protruding from the patch body to directly deliver a drug through stratum corneum of the skin to inner tissues of the skin. The microneedle includes light grooves in a concave shape disposed along a length direction of the microneedle in such a manner that therapeutic light radiated from a light source for phototherapy easily penetrates into the skin along the microneedle. The microneedle in which the light grooves are formed may be prepared by being combined with the patch body in various ways. Hereinafter, various embodiments of the phototherapeutic needle patch according to the technical idea of the present invention are presented.

Figure 2:
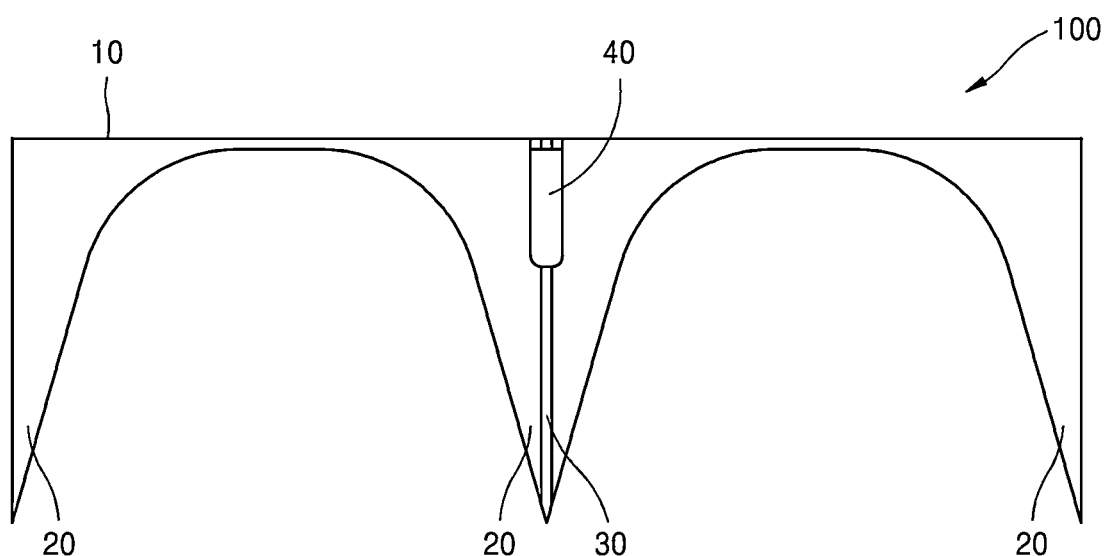
FIG. 2 is a side elevational view of the phototherapeutic needle patch of FIG. 1.
Figure 3:
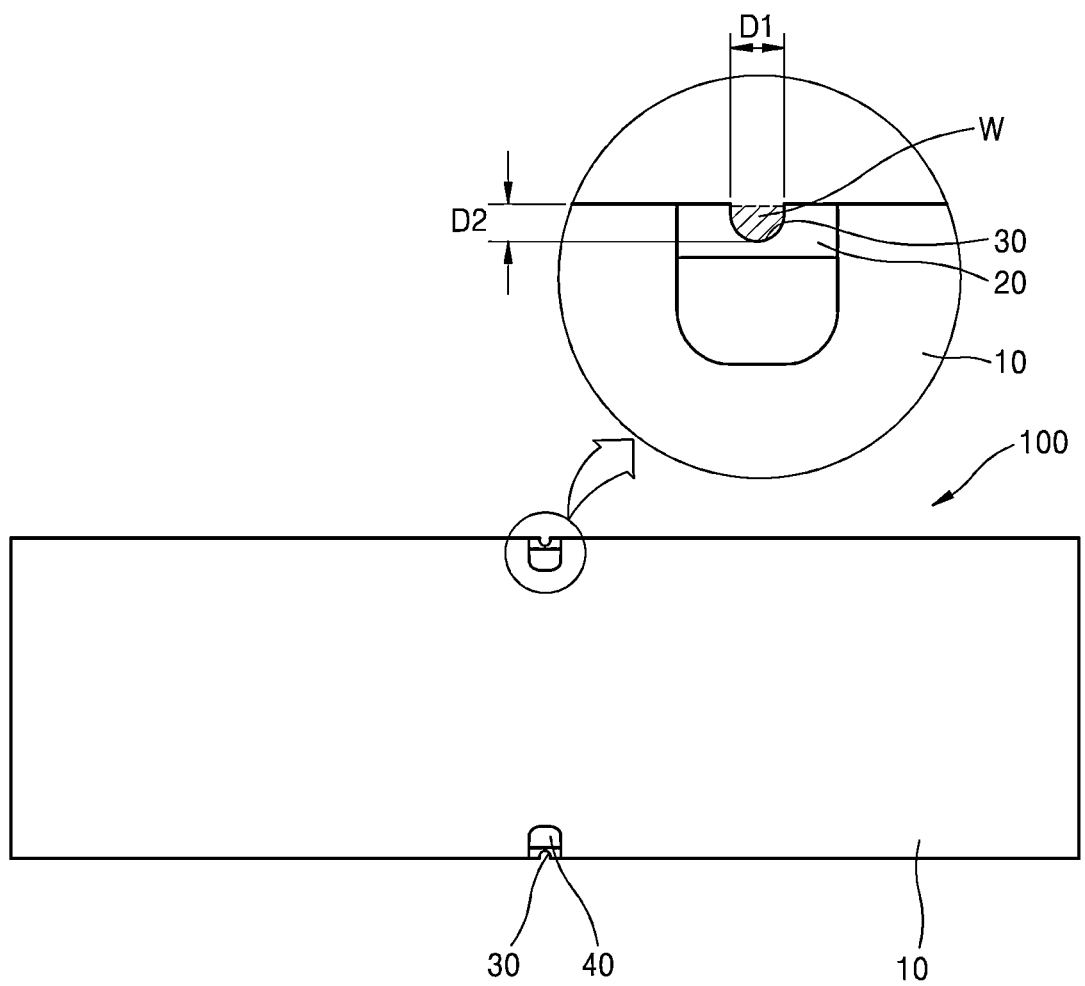
FIG. 3 is a top plan view of the phototherapeutic needle patch of FIG. 1.
Figure 4:
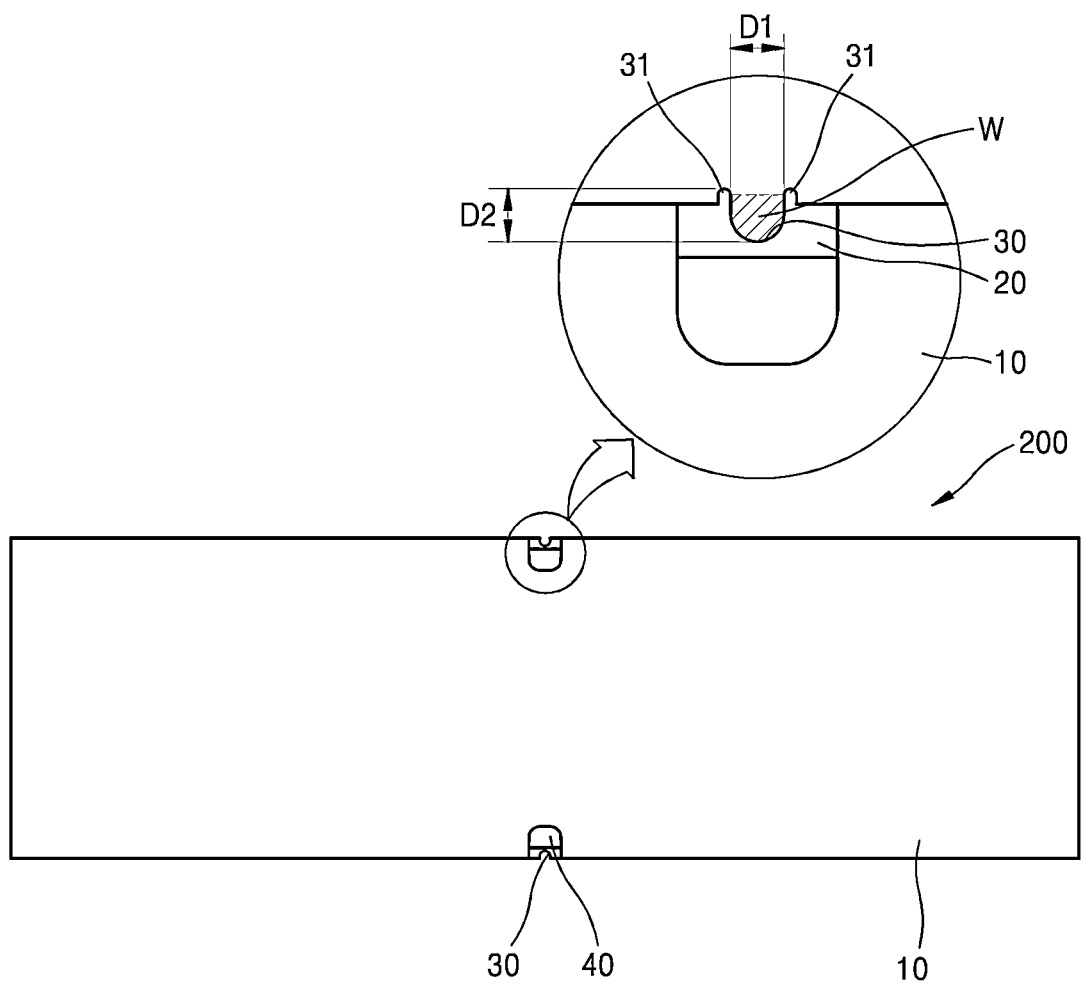
FIG. 4 is a top plan view of the phototherapeutic needle patch of FIG. 1.
Figure 5:
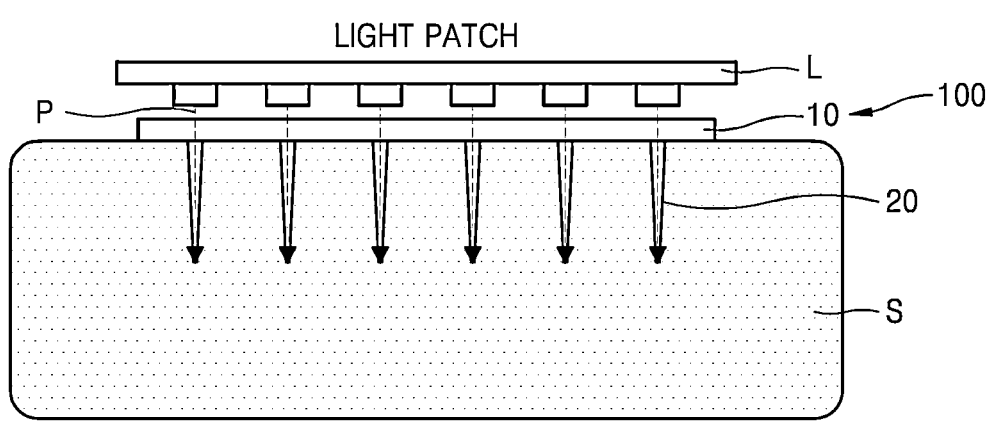
FIG. 5 is a cross-sectional view showing that phototherapy is performed by attaching a light patch to the phototherapeutic needle patch of FIG. 1.

FIG. 1 is a perspective view of a phototherapeutic needle patch 100 according to an embodiment of the present invention. FIG. 2 is a side elevational view of the phototherapeutic needle patch of FIG. 1, FIG. 3 is a top plan view of the phototherapeutic needle patch of FIG. 1, and FIG. 4 is a top plan view to 4 are schematic views of the phototherapeutic needle patch of FIG. 1. FIG. 5 is a cross-sectional view showing that phototherapy is performed by attaching a light patch L to the phototherapeutic needle patch 100 of FIG. 1, and FIGS. 6A, 6B, 7A and 7B are graphs showing the intensity of light P penetrating into the skin S when phototherapy is performed using the phototherapeutic needle patch 100 of FIG. 1.

Initially, as illustrated in FIG. 1, the phototherapeutic needle patch 100 according to an embodiment of the present invention may include a patch body 10, microneedles 20, light grooves 30, and slots 40.

As illustrated in FIGS. 1 to 5, the patch body 10 may have a flat panel shape so as to be attachable to the skin S of a patient. Specifically, the patch body 10 may have a thin rectangular plate shape and a plurality of microneedles 20 may protrude from a surface of the patch body 10.

As described above, the patch body 10 and the microneedles 20 may be formed as one body and be made of the same material. For example, the patch body 10 and the microneedles 20 may be made of a metal material which is harmless to be used for human bodies, e.g., one or more of titanium, titanium alloy, stainless steel, cobalt-chromium alloy, zinc, zinc alloy, magnesium, and magnesium alloy.

The patch body 10 in the thin rectangular plate shape may have flexibility so as to be naturally deformed and adhered according to the shape and curves of the skin S of a human body like a dynamic compression plate (DCP). An adhesive sheet may be provided on a surface of the patch body 10 in contact with the skin S to more firmly adhere the patch body 10 to the skin S of the human body.

As illustrated in FIGS. 1 to 3, the plurality of microneedles 20 may be formed at the thin-plate-shaped patch body 10 to deliver a drug W through the stratum corneum of the skin S to inner tissues of the skin S.

Specifically, the microneedles 20 may be gradually reduced in width from bases connected to the patch body 10 toward tips in a pointed shape to easily penetrate through the stratum corneum of the skin S. As described above, the microneedles 20 may have a cone shape, triangular pyramid shape, or quadrangular pyramid shape having a pointed tip, and may not be limited to any particular shape as long as the microneedles 20 may penetrate through the stratum corneum of the skin S. Although six microneedles 20 are illustrated along both sides of the patch body 10 in the current embodiment, the number of microneedles 20 may vary depending on the area or shape of the skin S to which the phototherapeutic needle patch 100 is attached.

The drug W may be coated on surfaces of the microneedles 20 or be filled in grooves formed in one-side surfaces of the microneedles 20 so as to penetrate into the skin S together with the microneedles 20.

The drug W penetrating into the skin S together with the microneedles 20 may be a sort of physiologically active substance. The physiologically active substance may refer to a compound or molecules applied to a host, animal, or human being to induce biological reaction, and include, for example, a therapeutic substance such as a vaccine, antibody, antitumor agent, insulin, painkiller, or hair loss solution, or a cosmetic substance such as retinol having anti-aging and whitening effects.

Alternatively, the physiologically active substance may include a lipolysis substance for losing weight or a non-therapeutic substance such as an anesthetic.

As described above, the drug W which is a sort of physiologically active substance may be provided in the form of an electrolyte or non-electrolyte solution or gel, and be coated on surfaces of the microneedles 20 or be filled in grooves formed in one-side surfaces of the microneedles 20. In the present invention, because the grooves may be used as optical paths through which therapeutic light passes for phototherapy, the drug W may be filled in the grooves of the microneedles 20. To allow the therapeutic light to easily pass through the grooves, the grooves may be filled with a transparent drug.

As described above, the grooves may serve as the light grooves 30 through which the therapeutic light P passes and, specifically, as illustrated in FIGS. 1 to 5, the light grooves 30 may be formed in a concave shape along a length direction of the microneedles 20 in such a manner that the therapeutic light P radiated from a light source L for phototherapy may easily penetrate into the skin S along the microneedles 20.

In this case, portions of the patch body 10 and portions of the microneedles 20 may be pierced in a slot shape to form the slots 40 connected to ends of the light grooves 30, in such a manner that the therapeutic light P radiated from the light source L may easily reach the light grooves 30 formed in the microneedles 20.

Therefore, the therapeutic light P radiated from the light source L may reach the ends of the light grooves 30 through portions connected between the patch body 10 and the microneedles 20 and upper portions of the microneedles 20 and then reach the pointed tips of the microneedles 20 through the light grooves 30, thereby easily penetrating deeply into the skin S.

The light grooves 30 may be formed in one or more of the plurality of the microneedles 20 connected to the patch body 10. For example, depending on an amount of the drug W injected through the microneedles 20 or an area requiring phototherapy, the light grooves 30 may be formed in all microneedles 20 or be selectively formed in some microneedles 20. In this case, the light grooves 30 may have a length equal to the length of the microneedles 20, or the length of the microneedles 20 and the length of the light grooves 30 may be determined together based on an effective penetration depth per wavelength of the therapeutic light P.

The above-described light grooves 30 may be formed by grooving the microneedles 20 in a thickness direction by using laser processing. However, the present invention is not limited thereto and the light grooves 30 may be formed by etching the microneedles 20 in the thickness direction by using chemical processing, or by grooving the microneedles 20 in the thickness direction by using physical machining.

As described above, the light grooves 30 processed along the length direction of the microneedles 20 may not only form the optical paths of the therapeutic light P radiated from the light source L but also contain the drug W as illustrated in FIG. 3.

When the microneedles 20 are inserted into the skin S, the skin S may be pushed into the light grooves 30. In this case, the light grooves 30 may be filled with the skin S and thus the optical paths of the therapeutic light P may not be formed. As such, to prevent the skin S from being pushed into the light grooves 30, the light grooves 30 may have a width D1 less than a depth D2. Therefore, because the light grooves 30 are formed in a narrow and sufficiently deep shape, even when the skin S is pushed into the light grooves 30, the skin S may be induced to fill only partial regions of the light grooves 30 and thus the optical paths through which the therapeutic light P passes may be maintained.

As illustrated in FIG. 4, for the phototherapeutic needle patch 200, when the light grooves 30 are formed using the laser processing, a condition for the laser processing may be controlled in such a manner that protrusions 31 protruding from both sides of the light grooves 30 are formed due to solidification of a metal material melted in the vicinity of the light grooves 30.

As described above, by forming the protrusions 31 at both sides of the light grooves 30 by controlling the condition for the laser processing, the depth D2 of the light grooves 30 may be much greater than the width D1 thereof. Therefore, the light grooves 30 may be formed in a narrow and deeper shape and thus the skin S may be effectively prevented from being pushed into the light grooves 30.

As such, as illustrated in FIG. 5, when the phototherapeutic needle patch 100 is attached to the skin S and then the light patch L having a plurality of light source is attached thereto for a combination of medication and phototherapy, the therapeutic light P radiated from the light patch L may be induced to penetrate deeply into the skin S along the microneedles 20.

Figure 6A:
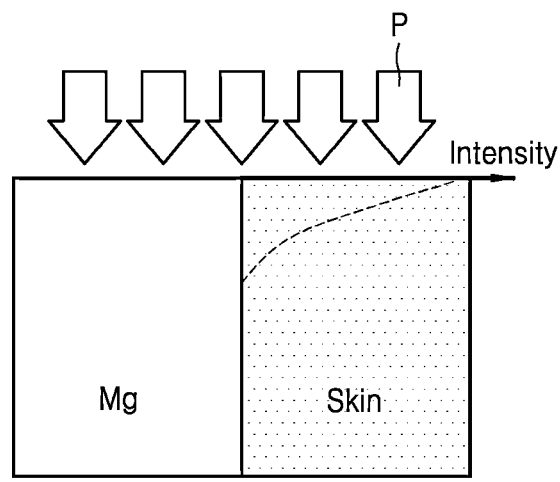
FIGS. 6A, 6B, 7A and 7B are graphs showing the intensity of light penetrating into the skin when phototherapy is performed using the phototherapeutic needle patch of FIG. 1.
Figure 6B:
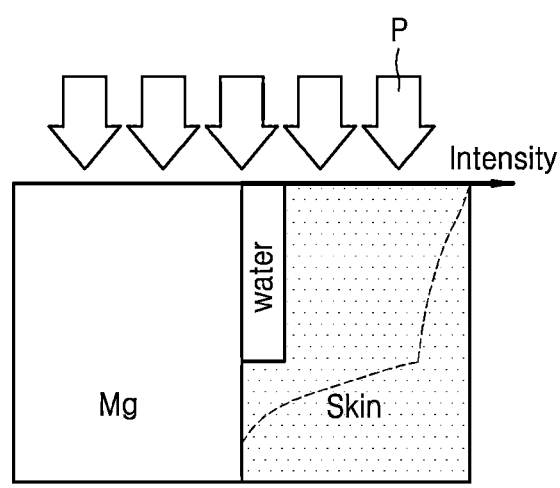
Figure 7A:
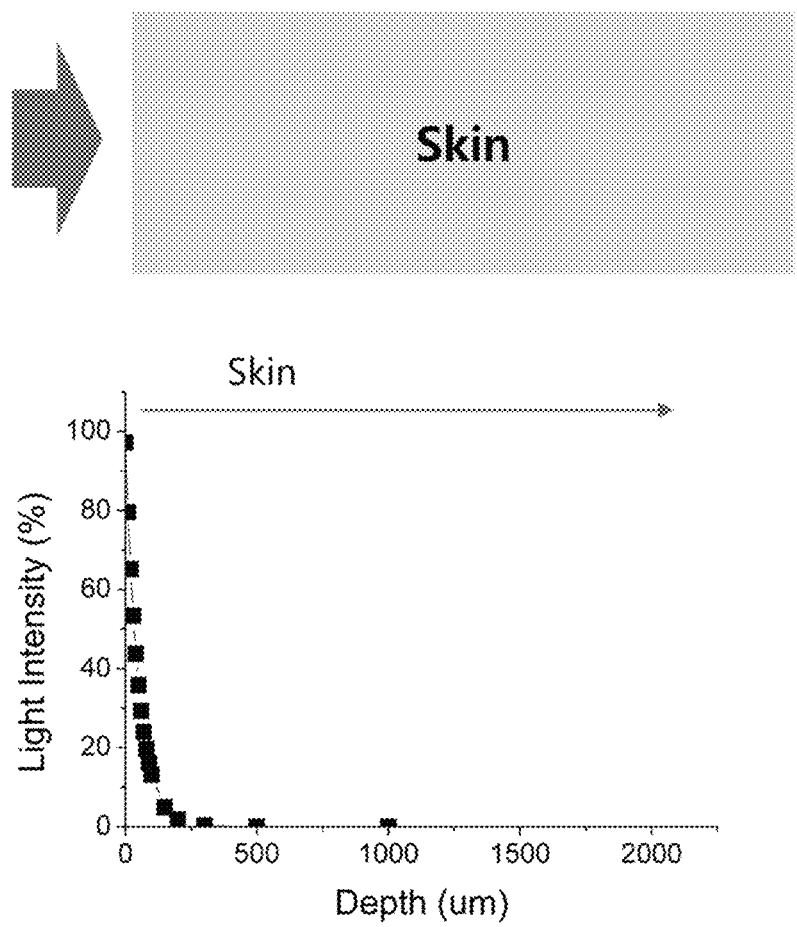
Figure 7B:
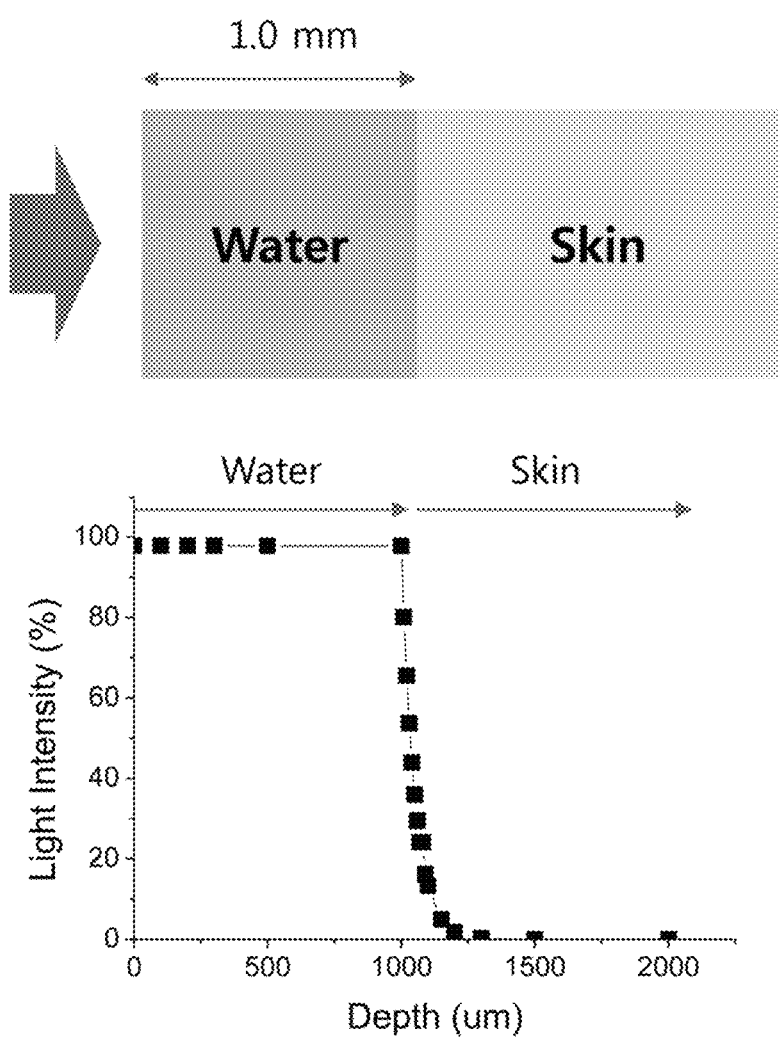

For example, although an effective penetration depth of the therapeutic light P radiated from the light patch L differs depending on a wavelength thereof, because an effective penetration depth of general visible light into the skin S is known to be up to about 500 μm, as illustrated in FIG. 6A and FIG. 7A, the therapeutic light P may not penetrate deeply into the skin S when the light grooves 30 are not formed in the microneedles 20. However, when the light grooves 30 are formed in the microneedles 20 and are used as optical paths according to the present invention to solve the above-described problem, as illustrated in FIG. 6B and FIG. 7B, the therapeutic light P may penetrate deeply into the skin S through the drug W filled in the light grooves 30.

Therefore, based on the phototherapeutic needle patches 100 and 200 according to various embodiments of the present invention, by forming the light grooves 30 in the microneedles 20 and using the same as optical paths, a penetration depth of the therapeutic light P, which has a wavelength equal to or less than that of visible light, into the skin S may be increased to be equal to or greater than a depth of the microneedles 20. Accordingly, the therapeutic light P may effectively penetrate into inner tissues of the skin S together with the drug W and thus a therapeutic effect for a patient may be maximized due to interaction between medication and phototherapy.

FIGS. 8 to 12 are sequential perspective views for describing a method of manufacturing the phototherapeutic needle patch 100, according to another embodiment of the present invention.

Figure 8:
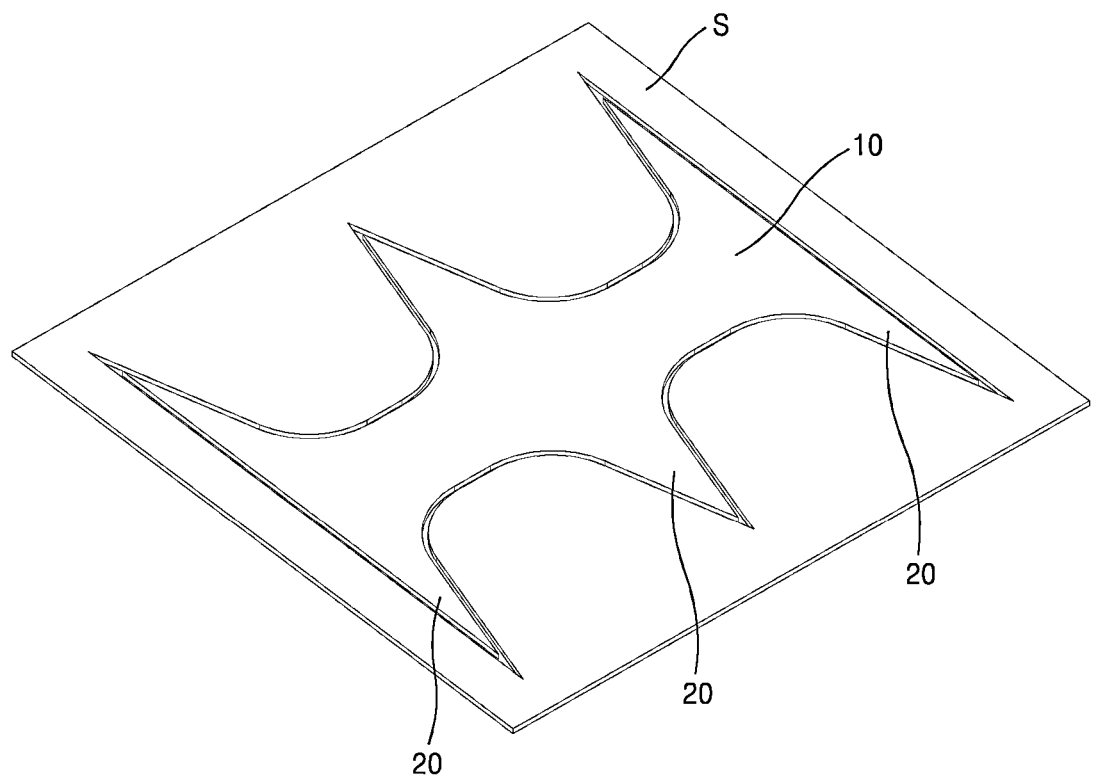
FIGS. 8 to 12 are sequential perspective views for describing a method of manufacturing a phototherapeutic needle patch, according to another embodiment of the present invention.

Based on the method according to another embodiment of the present invention, initially, as illustrated in FIG. 8, in a blanking step, a planar shape of the patch body 10 and the microneedles 20 may be formed by blanking out a certain shape from a plate-shaped material S.

For example, the planar shape of the patch body 10 and the microneedles 20 may be formed by pressing, laser-processing, or etching the plate-shaped material S. Although a planar shape for one phototherapeutic needle patch 100 is processed from the material S in the current embodiment, the present invention is not limited thereto and planar shapes for a plurality of phototherapeutic needle patches 100 may be simultaneously processed for mass production.

Figure 9:
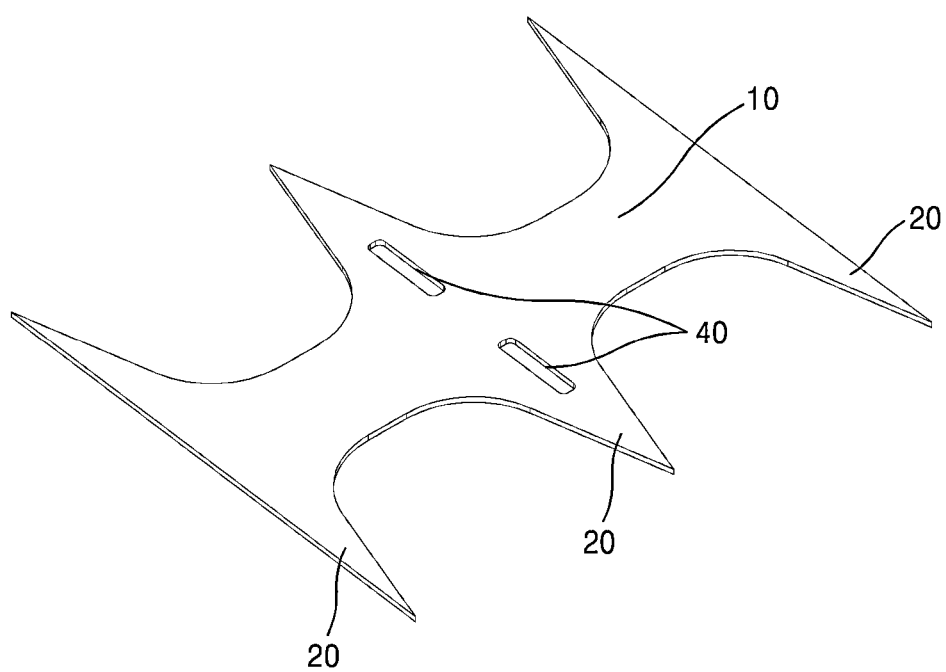
Figure 10:
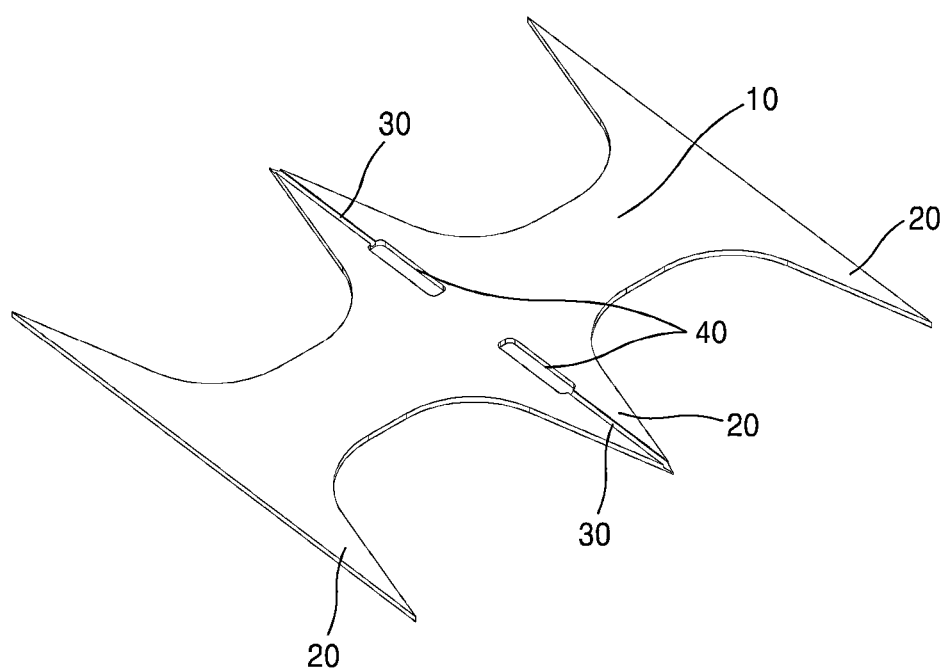

Then, the light grooves 30 and the slots 40 may be formed by piercing portions of the patch body 10 and portions of the microneedles 20 in a slot shape as illustrated in FIG. 9 and processing the light grooves 30 along a length direction of the microneedles 20 as illustrated in FIG. 10.

Figure 11:
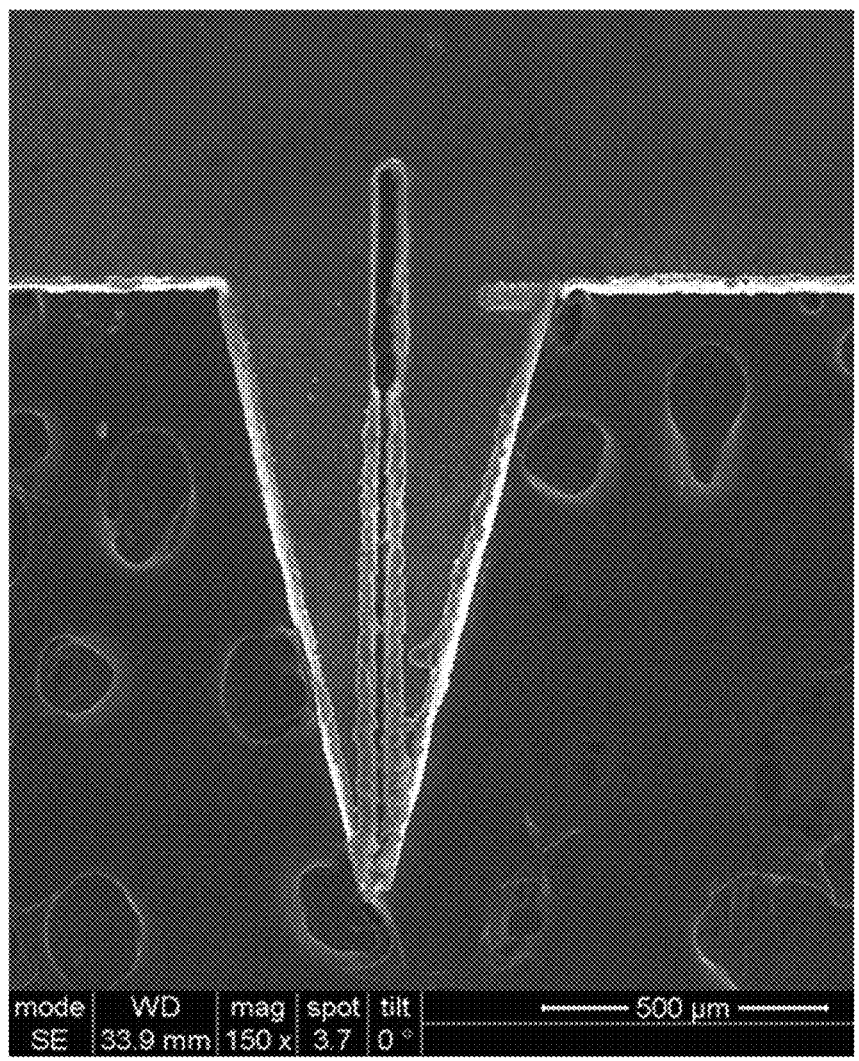

At this time, in the light groove forming step, the light grooves 30 may be formed by grooving the microneedles 20 in a thickness direction by using laser processing as shown in FIG. 11. However, the present invention is not limited thereto and the light grooves 30 may be formed by etching the microneedles 20 in the thickness direction by using chemical processing, or by grooving the microneedles 20 in the thickness direction by using physical machining.

Figure 12:
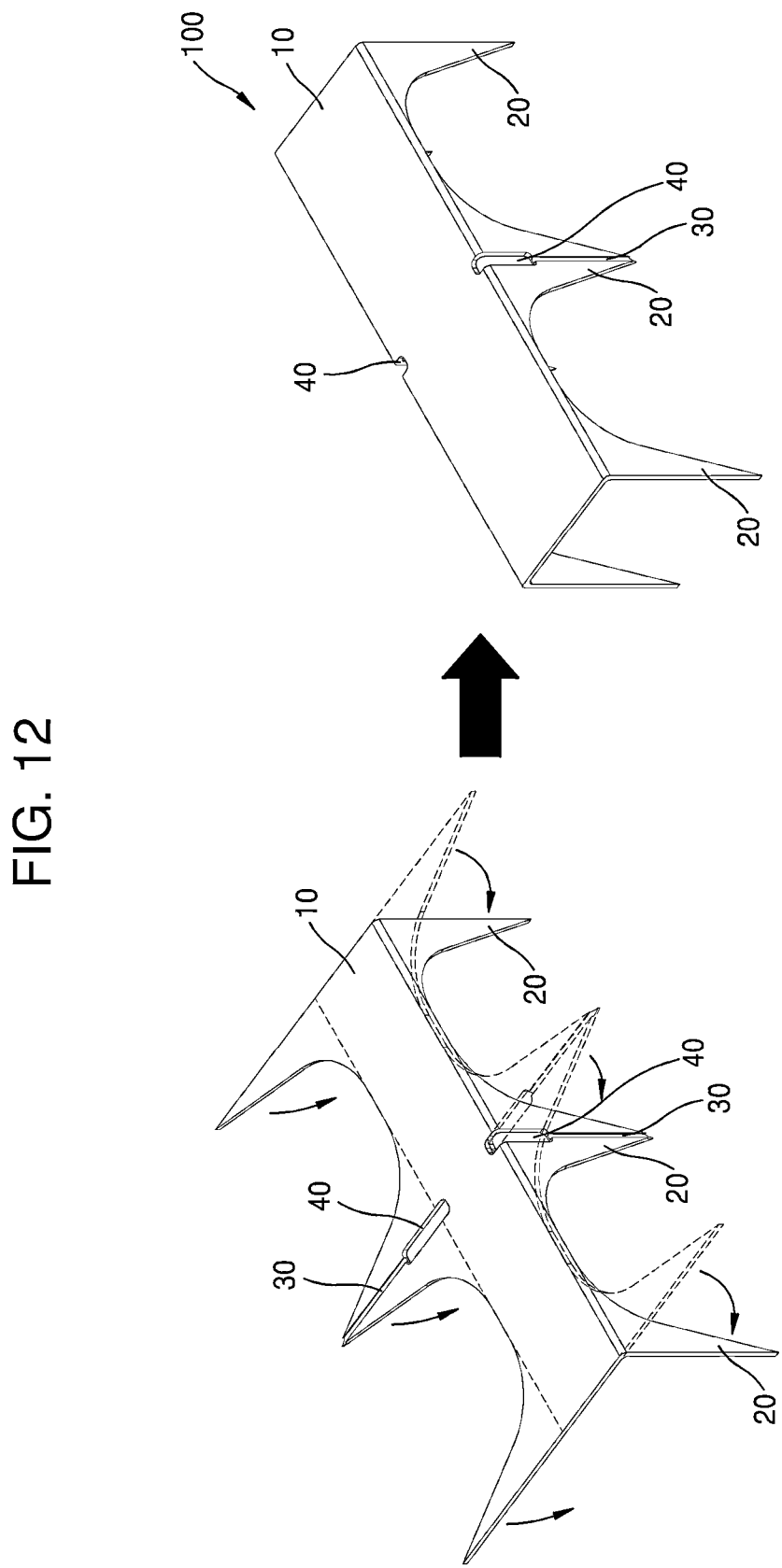

Then, the phototherapeutic needle patch 100 may be manufactured by forming the microneedles 20 in a direction perpendicular to the patch body 10 by bending portions connected between the patch body 10 and the microneedles 20 as illustrated in FIG. 12.

Therefore, based on the method according to another embodiment of the present invention, when the phototherapeutic needle patch 100 is manufactured, by forming the light grooves 30 and the slots 40 in the microneedles 20 and using the same as optical paths of the therapeutic light P, a penetration depth of the therapeutic light P, which has a wavelength equal to or less than that of visible light, into the skin S to perform phototherapy by using the phototherapeutic needle patch 100 may be increased to be equal to or greater than a depth of the microneedles 20. Accordingly, the therapeutic light P may effectively penetrate into inner tissues of the skin S together with the drug W and thus the phototherapeutic needle patch 100 capable of maximizing a therapeutic effect for a patient due to interaction between medication and phototherapy may be easily manufactured.

As described above, according to an embodiment of the present invention, phototherapeutic needle patches capable of inducing a drug to effectively and rapidly penetrate into inner tissues of the skin, and of inducing light to effectively penetrate into the inner tissues of the skin together with the drug through optical paths formed in needle surfaces to maximize a therapeutic effect for a patient due to interaction between medication and phototherapy, and methods of manufacturing the same may be implemented. However, the scope of the present invention is not limited to the above-described effects.

In addition, the shape of the patch body and the microneedle of the phototherapeutic needle patch are not necessarily limited to the above-described embodiments and may have various shapes.

Figure 13:
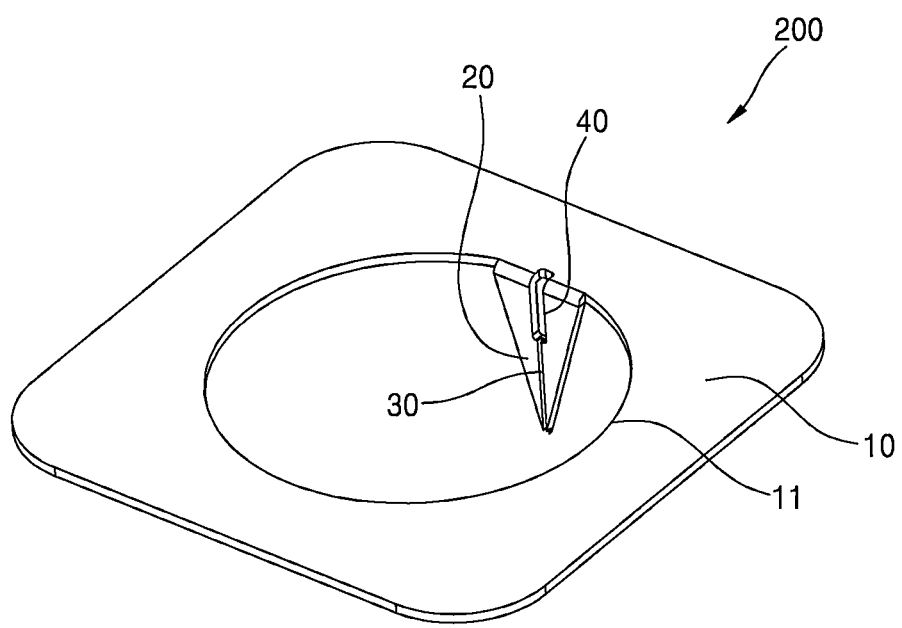
FIG. 13 is a perspective view schematically showing a phototherapeutic needle patch according to yet another embodiment of the present invention.
Figure 14:
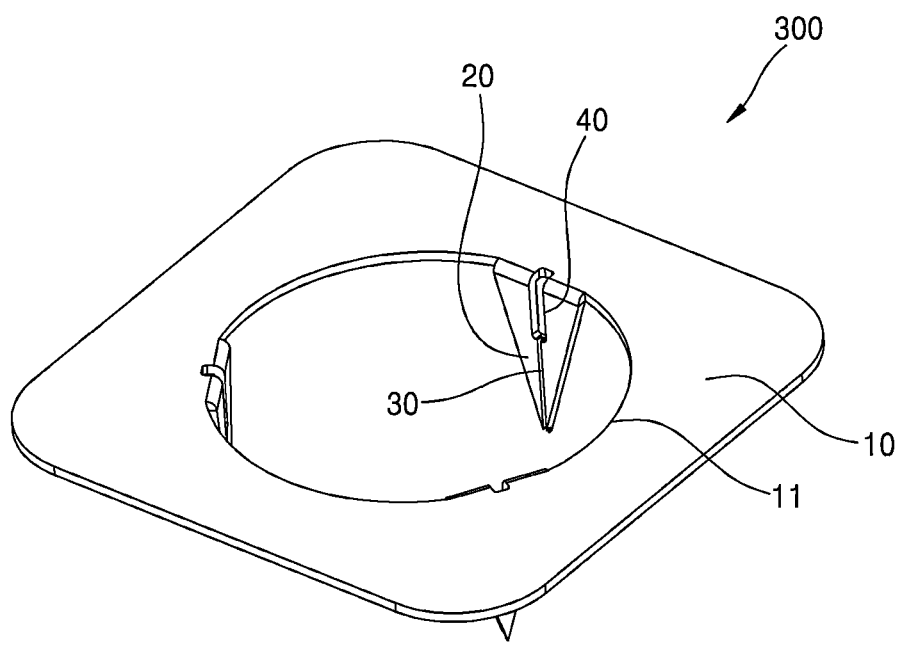
FIG. 14 is a plan perspective view schematically showing a phototherapeutic needle patch according to yet another embodiment of the present invention.
Figure 15:
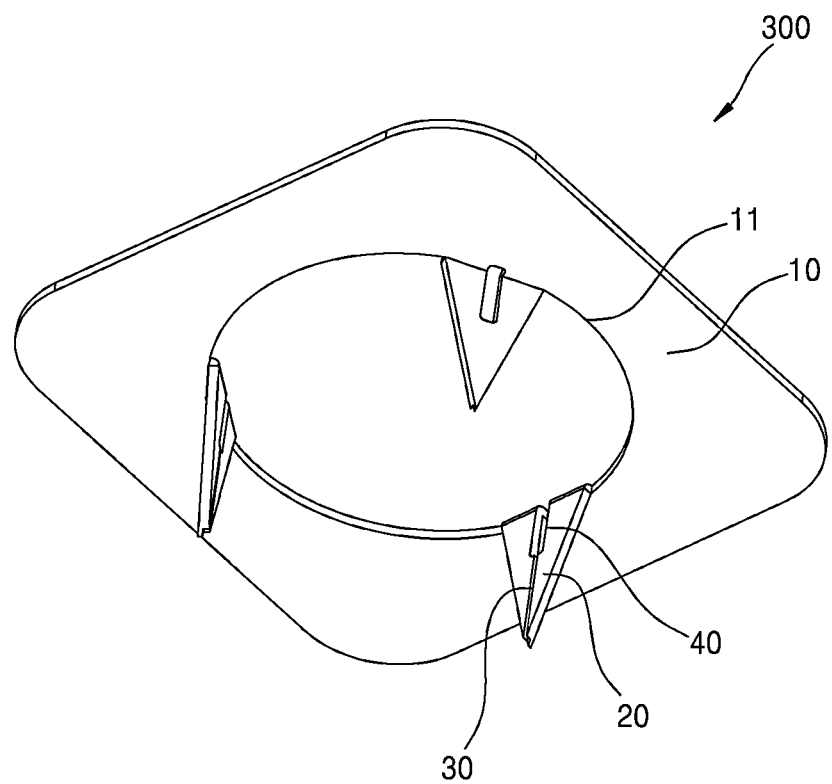
FIG. 15 is a bottom perspective view schematically showing a phototherapeutic needle patch according to yet another embodiment of the present invention.
Figure 16:
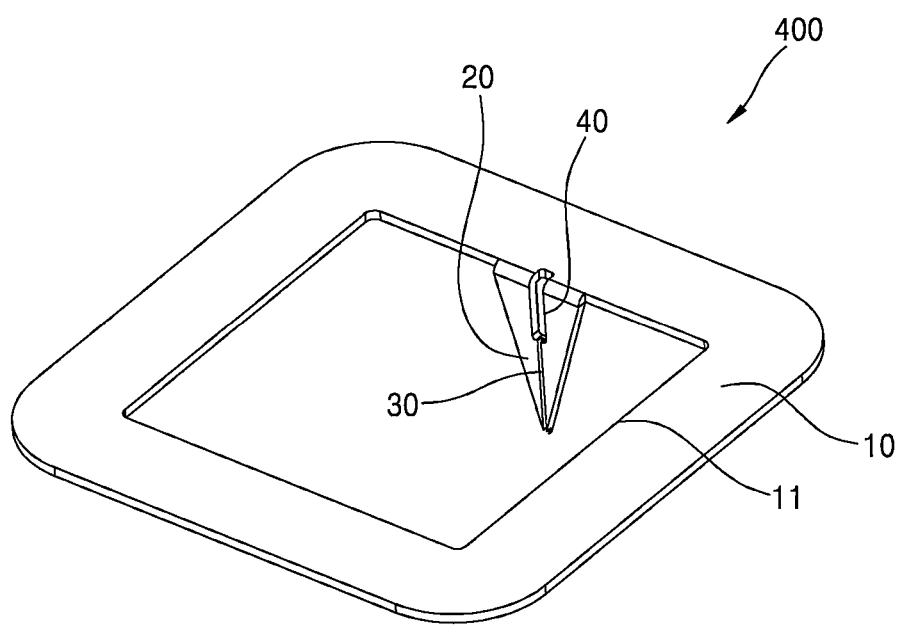
FIG. 16 is a perspective view schematically showing a phototherapeutic needle patch according to yet another embodiment of the present invention.
Figure 17:
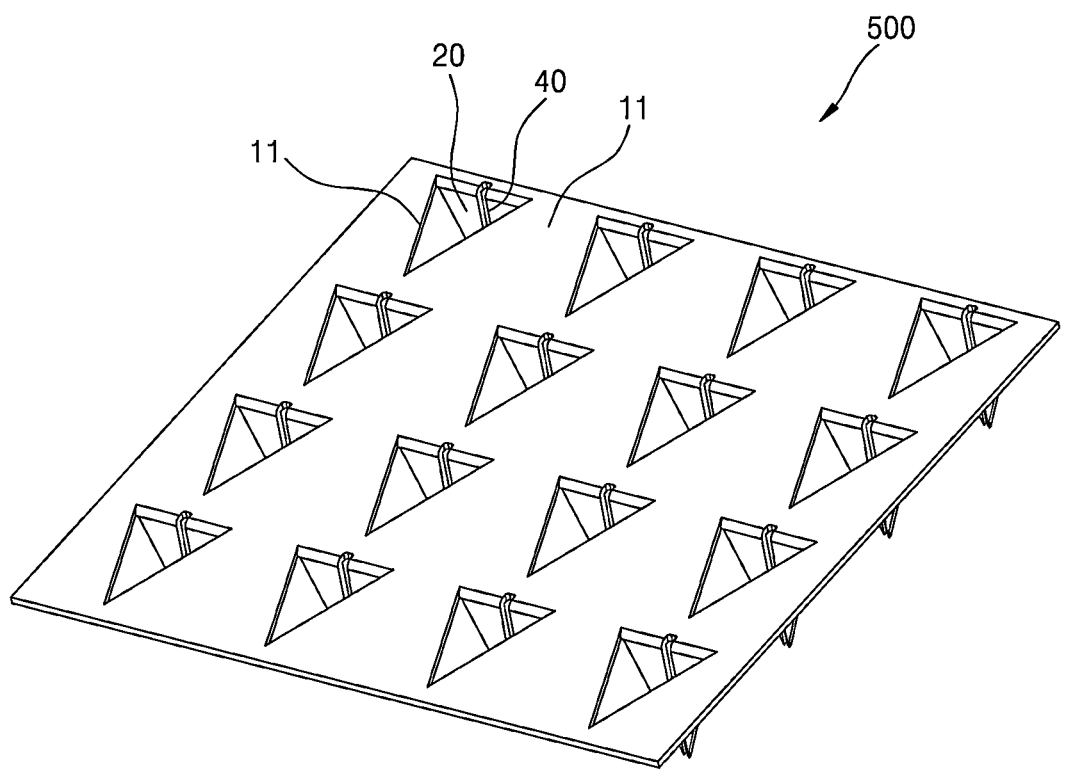
FIG. 17 is a plan perspective view schematically showing a phototherapeutic needle patch according to yet another embodiment of the present invention.
Figure 18:
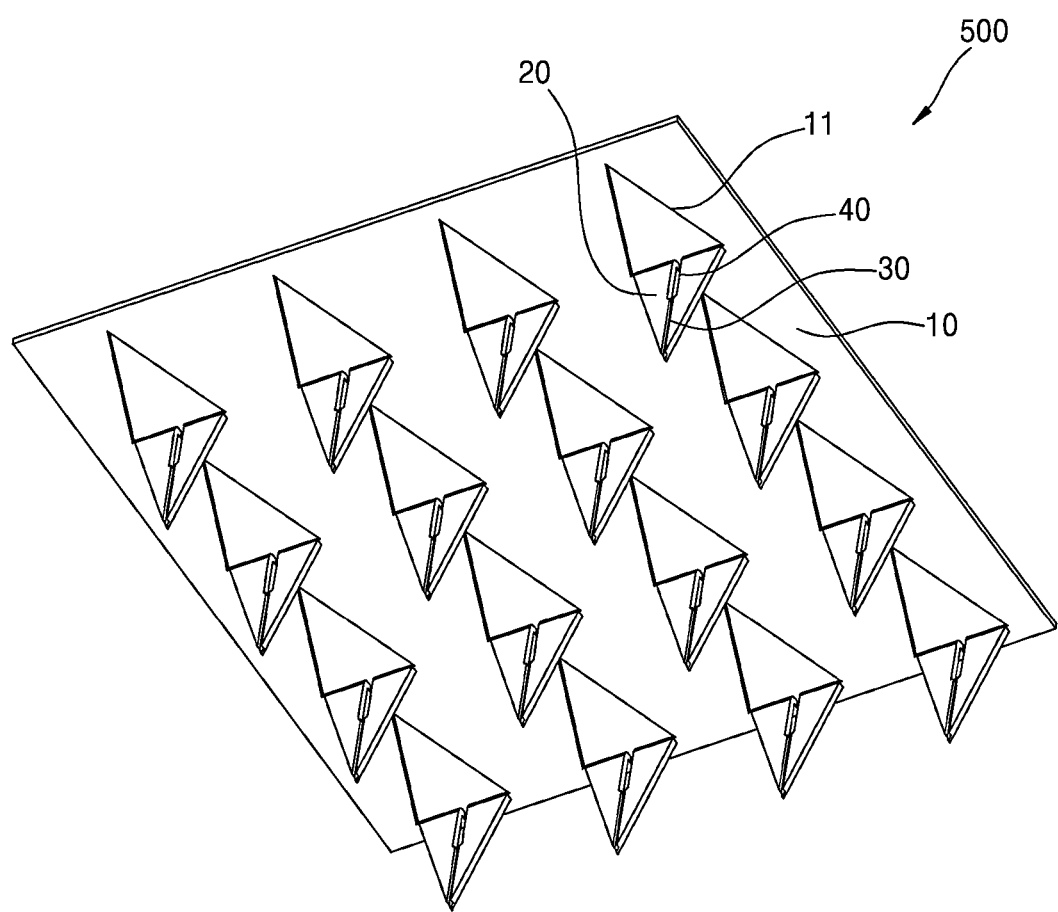
FIG. 18 is a bottom perspective view schematically showing a phototherapeutic needle patch according to yet another embodiment of the present invention.

FIG. 13 is a perspective view schematically showing a phototherapeutic needle patch according to yet another embodiment of the present invention. FIG. 14 is a plan perspective view schematically showing a phototherapeutic needle patch 300 according to yet another embodiment of the present invention, and FIG. 15 is a bottom perspective view schematically showing the phototherapeutic needle patch 300 according to yet another embodiment of the present invention. Furthermore, FIG. 16 is a perspective view schematically showing a phototherapeutic needle patch 400 according to yet another embodiment of the present invention. FIG. 17 is a plan perspective view schematically showing a phototherapeutic needle patch 500 according to yet another embodiment of the present invention, and FIG. 18 is a bottom perspective view schematically showing the phototherapeutic needle patch 500 according to yet another embodiment of the present invention.

First, as shown in FIG. 13, the microneedle 20 of the phototherapeutic needle patch 200 can be formed by bending at least a part of the patch body 10 at a side of the through hole 11 formed in a circular shape in the patch body 10.

For example, when forming the through hole 11 in the patch body 10, the through hole 11 may be formed to penetrate the patch body 10 in a circular shape except for a portion to be bent later to become the microneedle 20. Accordingly, a triangular protrusion may be formed in the through hole 11 of the patch body 10.

Subsequently, by bending the triangular protrusion formed in the through hole 11 downward from the patch body 10, the microneedle 20 having a pointed tip in a vertical shape from the patch body 10 may be formed.

Here, it was illustrated that one microneedle 20 is formed on the patch body 10, but the present invention is not necessarily limited to what is shown in FIG. 13. Instead, in the phototherapeutic needle patch 300 according to yet another embodiment of the present invention as shown in FIGS. 14 and 15, a plurality of microneedles 20 may be formed along the through hole 11 of the patch body 10.

Furthermore, the shape of the through hole 11 of the patch body 10 is also not necessarily limited to what is shown in FIG. 13. Instead, in the phototherapeutic needle patch 400 according to yet another embodiment of the present invention as shown in FIG. 16, the through hole 11 may be formed in a square shape. The through hole 11 may also be formed in a wide variety of shapes such as a triangular shape, a hexagonal shape, or an octagonal shape.

Furthermore, in the phototherapeutic needle patch 500 according to another embodiment of the present invention as shown in FIGS. 17 and 18, a plurality of microneedles 20 may be formed in a predetermined pattern on the patch body 10.

For example, the microneedles 20 may be formed in a pattern having a plurality of square-shaped arrangements on the patch body 10. More specifically, the microneedles 20 may be formed by cutting, by mechanical processing such as laser cutting or notching, the portion corresponding to the two sides of equal length of the microneedle 20 in the form of an isosceles triangle from the patch body 10, and then by bending the cut portion downward from the patch body 10, such that the microneedle is formed in a vertical shape from the patch body 10 with a sharp tip. Accordingly, the patch body 10 may be formed with a through hole 11 having an isosceles triangle shape.

Here, although the plurality of microneedles 20 have been illustrated as being formed in a pattern having a rectangular arrangement on the patch body 10, it is not limited thereto. Instead, it may be formed in a pattern having various types of arrangement.

The light grooves 30 and the through hole 40 of the phototherapeutic needle patch 200, 300, 400, and 500 according to the above-described embodiments may be formed by the same process as the manufacturing method of the phototherapeutic needle patch 100 according to the embodiment of the present invention as shown in FIGS. 8 to 12. Therefore, detailed description thereof will be omitted.

While the present invention has been particularly shown and described with reference to embodiments thereof, it will be understood by one of ordinary skill in the art that various changes in form and details may be made therein without departing from the scope of the present invention as defined by the following claims.

What is claimed is:

1. A phototherapeutic needle patch comprising:
    a patch body configured to be attachable to skin of a patient;
    at least one microneedle protruding from the patch body, one end of each of the at least one microneedle configured to deliver a drug through stratum corneum of the skin to inner tissues of the skin; and
    light grooves in a concave shape disposed along a length direction of the at least one microneedle in such a manner that therapeutic light radiated from a light source for phototherapy penetrates into the skin along the at least one microneedle,
    wherein the patch body comprises an adhesive sheet on a surface in contact with the skin so as to be adherable to the skin.

2. The phototherapeutic needle patch of claim 1, wherein the light grooves are disposed in one or more of the at least one microneedle.

3. The phototherapeutic needle patch of claim 1, wherein the at least one microneedle are gradually reduced in width from bases connected to the patch body toward tips in a pointed shape to penetrate through the stratum corneum of the skin.

4. The phototherapeutic needle patch of claim 1, wherein the light grooves are formed by grooving the at least one microneedle in a thickness direction by using laser processing.

5. The phototherapeutic needle patch of claim 4, wherein the light grooves have a width less than a depth to prevent tissues of the skin from filling the light grooves and blocking optical paths of the therapeutic light.

6. The phototherapeutic needle patch of claim 1, wherein the light grooves contain the drug.

7. The phototherapeutic needle patch of claim 1, wherein a plurality of microneedles is disposed along both sides of the patch body.

8. The phototherapeutic needle patch of claim 1, wherein the at least one microneedle is formed by bending at least a part of the patch body at a side of a through hole that is disposed in the patch body.

9. A phototherapeutic needle patch comprising:
    a patch body configured to be attachable to skin of a patient;
    at least one microneedle protruding from the patch body, one end of each of the at least one microneedle configured to deliver a drug through stratum corneum of the skin to inner tissues of the skin;
    light grooves in a concave shape disposed along a length direction of the at least one microneedle in such a manner that therapeutic light radiated from a light source for phototherapy penetrates into the skin along the at least one microneedle; and
    slots formed by piercing portions of the patch body and portions of the at least one microneedle in a slot shape and connected to ends of the light grooves in such a manner that the therapeutic light reaches the light grooves formed in the at least one microneedle.

10. A phototherapeutic needle patch comprising:
    a patch body configured to be attachable to skin of a patient;
    at least one microneedle protruding from the patch body, one end of each of the at least one microneedle configured to deliver a drug through stratum corneum of the skin to inner tissues of the skin; and
    light grooves in a concave shape disposed along a length direction of the at least one microneedle in such a manner that therapeutic light radiated from a light source for phototherapy penetrates into the skin along the at least one microneedle,
    wherein the light grooves comprise protrusions protruding from both sides of the light grooves.

* * * * *